United States Patent
Akagane

(10) Patent No.: US 10,368,896 B2
(45) Date of Patent: Aug. 6, 2019

(54) TREATMENT DEVICE

(71) Applicant: OLYMPUS CORPORATION, Hachioji-shi, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/269,175

(22) Filed: Sep. 19, 2016

(65) Prior Publication Data
US 2017/0000515 A1    Jan. 5, 2017

Related U.S. Application Data

(63) Continuation of application No. PCT/JP2015/063762, filed on May 13, 2015.

(30) Foreign Application Priority Data

May 23, 2014    (JP) .................................. 2014-107512

(51) Int. Cl.
*A61B 18/12* (2006.01)
*A61B 17/32* (2006.01)
(Continued)

(52) U.S. Cl.
CPC ...... *A61B 17/320068* (2013.01); *A61B 18/00* (2013.01); *A61B 18/12* (2013.01);
(Continued)

(58) Field of Classification Search
CPC . A61B 17/320068; A61B 18/00; A61B 18/12; A61B 2018/00083;
(Continued)

(56) References Cited

U.S. PATENT DOCUMENTS

2001/0012936 A1* 8/2001 Heim ................... A61B 18/14
606/45
2008/0234710 A1  9/2008 Neurohr et al.
(Continued)

FOREIGN PATENT DOCUMENTS

EP  0970659 A1  1/2000
EP  3103407 A1  12/2016
(Continued)

OTHER PUBLICATIONS

Nov. 29, 2016 International Preliminary Report on Patentability issued in International Application No. PCT/JP2015/063762.
(Continued)

*Primary Examiner* — Michael F Peffley
*Assistant Examiner* — Khadijeh A Vahdat
(74) *Attorney, Agent, or Firm* — Oliff PLC

(57) ABSTRACT

A treatment device includes, a probe that conveys ultrasonic vibration and a high-frequency current; a treatment section that comprises a first treatment surface provided at a distal end of the probe for treating body tissue and a second treatment surface opposed to the first treatment surface, and treats the body tissue with the ultrasonic vibration and the high-frequency current conveyed to the first treatment surface and the second treatment surface via the probe; and an electrically-insulating coating portion that covers at least one of the first treatment surface and the second treatment surface.

8 Claims, 4 Drawing Sheets

(51) Int. Cl.
*A61B 18/00* (2006.01)
*A61N 7/02* (2006.01)
*A61B 18/14* (2006.01)

(52) U.S. Cl.
CPC ...... *A61N 7/02* (2013.01); *A61B 2018/00083* (2013.01); *A61B 2018/00107* (2013.01); *A61B 2018/00607* (2013.01); *A61B 2018/00994* (2013.01); *A61B 2018/1412* (2013.01)

(58) Field of Classification Search
CPC .......... A61B 2018/00107; A61B 2018/00607; A61B 2018/00994; A61B 2018/1412; A61N 7/02
USPC ...................................... 606/27–50
See application file for complete search history.

(56) References Cited

U.S. PATENT DOCUMENTS

| | | |
|---|---|---|
| 2012/0239068 A1 | 9/2012 | Morris et al. |
| 2012/0277778 A1 | 11/2012 | Masuda et al. |
| 2014/0135804 A1 | 5/2014 | Weisenburgh, II et al. |

FOREIGN PATENT DOCUMENTS

| | | |
|---|---|---|
| JP | 2001-000446 A | 1/2001 |
| JP | 2004-290516 A | 10/2004 |
| JP | 2005-501609 A | 1/2005 |
| JP | 2009-050593 A | 3/2009 |
| JP | 2009-119209 A | 6/2009 |
| JP | 2010-522034 A | 7/2010 |
| JP | 2014-506148 A | 3/2014 |
| WO | 2008/118709 A1 | 10/2008 |
| WO | 2011/099571 A1 | 8/2011 |
| WO | 2015/020147 A1 | 2/2015 |

OTHER PUBLICATIONS

Jan. 26, 2016 Office Action issued in Japanese Patent Application No. 2015-558294.
Aug. 11, 2015 Search Report issued in International Patent Application No. PCT/JP2015/063762.
Feb. 26, 2018 Extended European Search Report issued in European Patent Application No. 15796822.3.

* cited by examiner

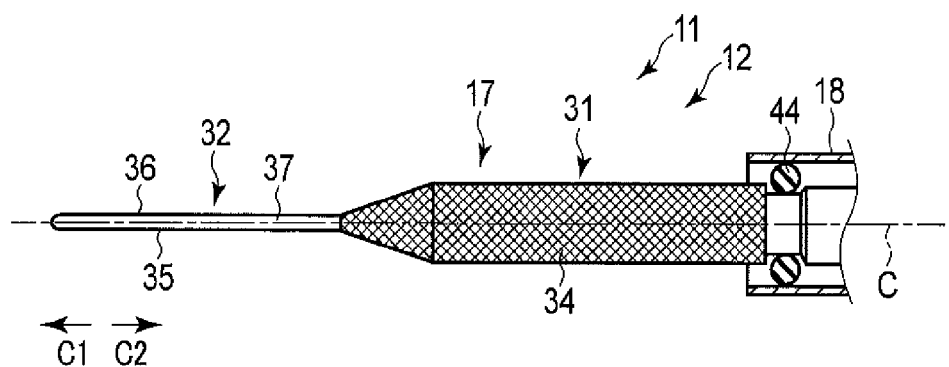
F I G. 5
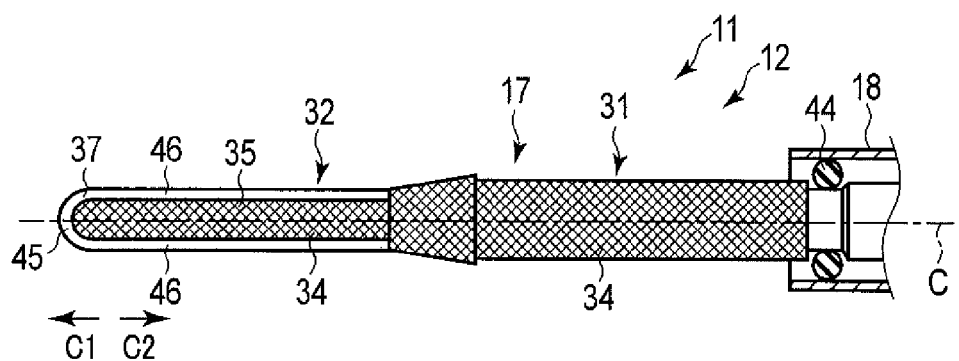
F I G. 6
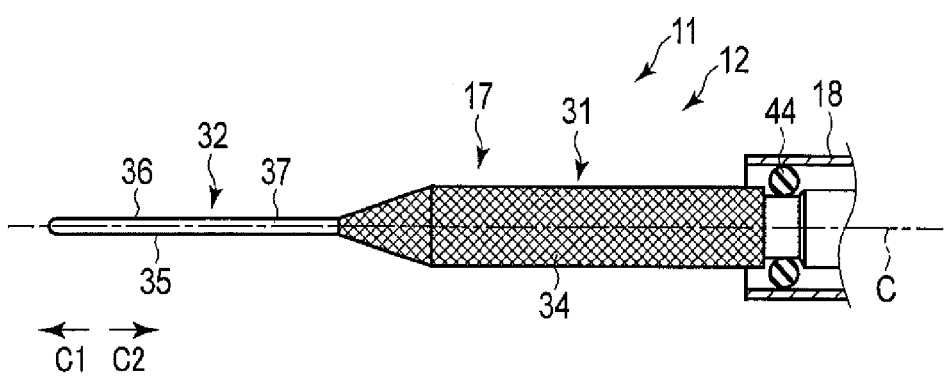
F I G. 7

TREATMENT DEVICE

CROSS-REFERENCE TO RELATED APPLICATIONS

This application is a Continuation application of PCT Application No. PCT/JP2015/063762, filed May 13, 2015 and based upon and claiming the benefit of priority from prior Japanese Patent Application No. 2014-107512, filed May 23, 2014, the entire contents of all of which are incorporated herein by reference.

BACKGROUND OF THE INVENTION

1. Field of the Invention

The present invention relates to a treatment device that treats body tissue with ultrasonic vibration.

2. Description of the Related Art

Jpn. Pat. Appln. KOKAI Publication No. 2005-501609 (Patent Literature 1) discloses a medical apparatus including jaws 18a and 18b at least a part (such as a part of the jaws 18a and 18b directly contacting electrodes 25a and 25b) of which is formed/manufactured from a non-conductive material.

Jpn. Pat. Appln. KOKAI Publication No. 2001-446 (Patent Literature 2) discloses a common treatment device. This treatment device includes a horn, and an insulating coating provided on an outer surface of the horn. The insulating portion is formed on the outer peripheral surface of the horn except for a part, which forms an exposed area.

BRIEF SUMMARY OF THE INVENTION

A treatment device comprises, a probe that conveys ultrasonic vibration and a high-frequency current; a treatment section that comprises a first treatment surface provided at a distal end of the probe for treating body tissue and a second treatment surface opposed to the first treatment surface, and treats the body tissue with the ultrasonic vibration and the high-frequency current conveyed to the first treatment surface and the second treatment surface via the probe; and an electrically-insulating coating portion that covers at least one of the first treatment surface and the second treatment surface.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 5 is a top view showing a probe of a treatment device of the second embodiment.

FIG. 6 is a side view showing the probe of the treatment device shown in FIG. 5.

FIG. 7 is a top view showing a probe of a treatment device of the third embodiment.

DETAILED DESCRIPTION OF THE INVENTION

First Embodiment

The first embodiment of the present invention will be described with reference to FIGS. 1 to 4.

Figure 1:
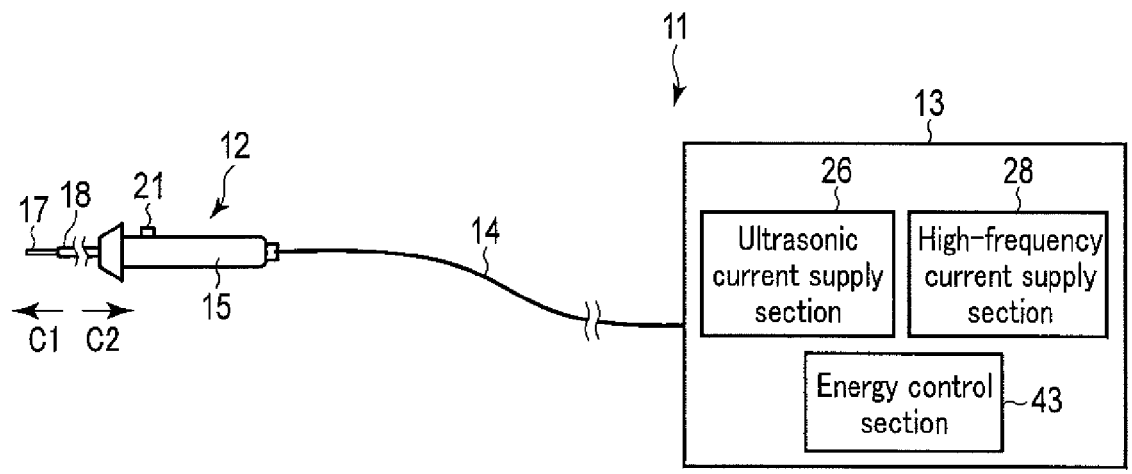
FIG. 1 is a schematic diagram showing the entire configuration of a treatment device of the first embodiment.

As shown in FIG. 1, the treatment device 11 includes a hand piece 12, a power source unit 13, and a cable 14 connecting the hand piece 12 and the power source unit 13.

Figure 2:
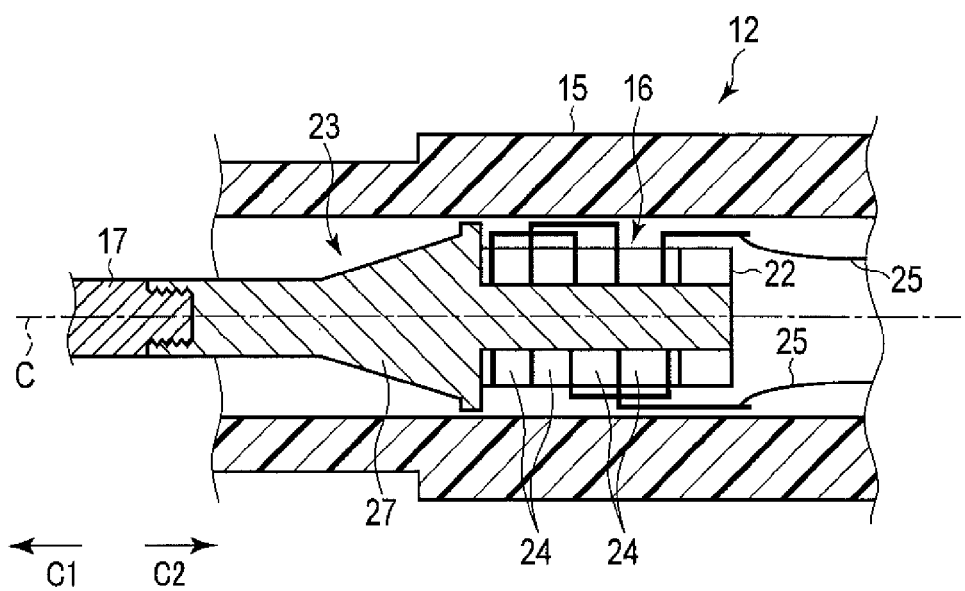
FIG. 2 is a cross-sectional view showing the surroundings of a vibration generation section of a hand piece of the treatment device shown in FIG. 1.

As shown in FIGS. 1 and 2, the hand piece 12 includes a holding portion 15 forming an outer shell, a vibration generation section 16 (transducer) contained in the holding portion 15, a probe 17 connected to the vibration generation section 16, and a cylindrical sheath 18 that covers the periphery of the probe 17 to protect the probe 17. The holding portion 15 is connected to one end of the cable 14. The other end of the cable 14 is connected to the power source unit 13. The holding portion 15 is, for example, cylindrical.

The holding portion 15 is provided with a energy operation input button 21. A doctor operates the energy operation input button 21 and can thereby apply energy (ultrasonic vibration and a high-frequency current), via the probe 17, to body tissue to be treated. Cushioning (elastic member) for absorbing vibration generated by the vibration generation section 16 may be provided between the inner peripheral surface of the holding portion 15 and the vibration generation section 16.

As shown in FIG. 2, the vibration generation section 16 includes an ultrasonic transducer 22 and a horn member 23. The ultrasonic transducer 22 is provided with a piezoelectric element 24 (four piezoelectric elements in the present embodiment) for changing a current into ultrasonic vibration. The ultrasonic transducer 22 is connected to one end of an electric line 25. The other end of the electric line 25 is connected to the ultrasonic current supply section 26 of the power source unit 13 through the cable 14. As power is supplied to the ultrasonic transducer 22 from the ultrasonic current supply section 26 via the electric line 25, ultrasonic vibration is generated in the ultrasonic transducer 22.

The ultrasonic transducer 22 is attached to the horn member 23. The horn member 23 is made of a metallic material. The horn member 23 is provided with an approximate cone-shaped cross-section transition portion 27, whose cross-sectional area decreases in a distal direction C1 of the probe 17. The ultrasonic vibration generated in the ultrasonic transducer 22 is conveyed to the horn member 23. The cross-section area transition portion 27 increases the amplitude of the ultrasonic vibration.

The probe 17 is formed into a rod of, for example, a biocompatible metallic material (such as titanium alloy). To the probe 17, ultrasonic vibration is conveyed from the vibration generation section 16, and a high-frequency current is supplied from the high-frequency current supply section 28. Therefore, the probe 17 not only applies ultrasonic vibration to body tissue, but also functions as a first electrode (active electrode) of a monopolar-type electrosurgical knife. The treatment device 11 of the present embodiment has a return electrode (not shown) that functions as a second electrode of the monopolar-type electrosurgical knife. The return electrode is connected to the high-frequency current supply section 28 via an electric line, and is provided in a position where the return electrode contacts a patient outside the patient's body at the time of surgery. In the present embodiment, one of the two directions parallel to the longitudinal axis C of the probe 17 is defined as a distal direction C1, and the opposite direction to the distal direction is defined as a proximal direction C2 (see FIG. 1).

Figure 3:
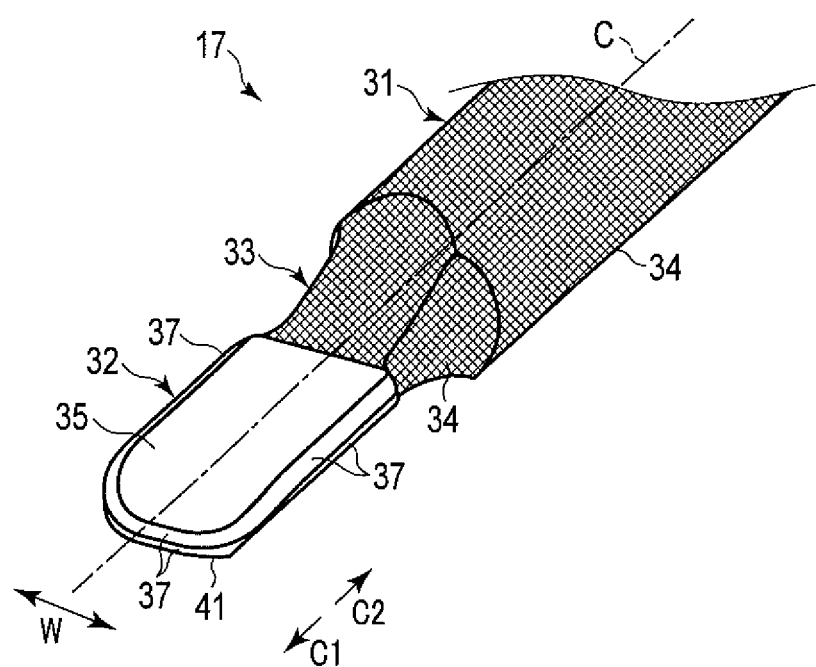
FIG. 3 is an enlarged perspective view of a treatment section of a probe of the treatment device shown in FIG. 1, which is viewed from a first treatment surface side.
Figure 4:
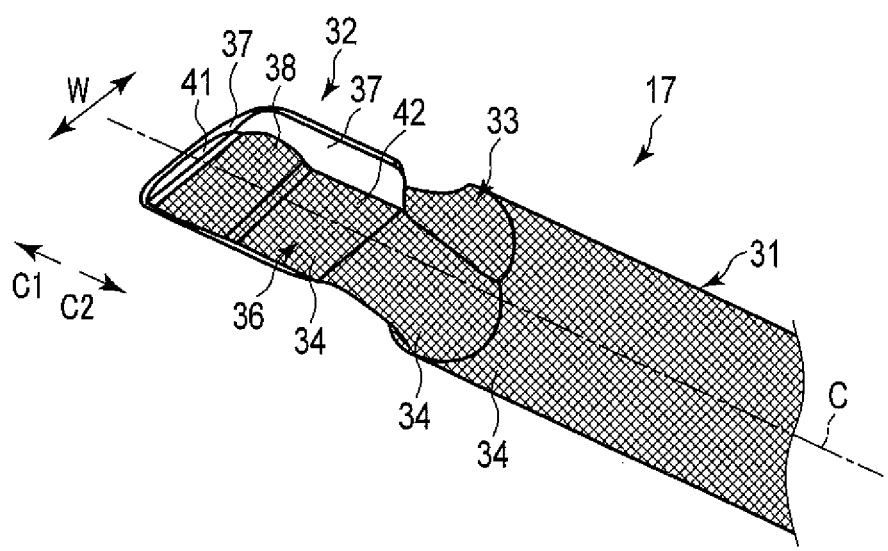
FIG. 4 is an enlarged perspective view of the treatment section of the probe of the treatment device shown in FIG. 3, which is viewed from a second treatment surface side.

The distal end part of the probe 17 protrudes from the distal end of the sheath 18. Namely, the sheath 18 covers a middle part of the probe 17 and the proximal end part opposite to the distal end part of the probe 17. As shown in FIGS. 3 and 4, the probe 17 includes a probe main body 31, a treatment section 32 formed on the distal end side of the probe main body 31 integral with the probe main body 31, a neck portion 33 provided between the probe main body 31 and the treatment section 32, and an insulating coating portion 34 that covers at least a part of the treatment section 32. The probe main body 31 is cylindrical (rod-shaped). The neck portion 33 has a dimension smaller than that of the treatment section 32 with respect to the width direction W intersecting the longitudinal axis C of the probe main body 31.

The treatment section 32 is shaped like a spoon or spatula. The treatment section 32 can treat body tissue with ultrasonic vibration and a high-frequency current conveyed via the probe main body 31. The treatment section 32 includes a first treatment surface 35, a second treatment surface 36 opposed to the first treatment surface 35, an outer peripheral portion 37 provided between the first treatment surface 35 and the second treatment surface 36 and adjacent to the first treatment surface 35 and the second treatment surface 36, a concave portion 38 formed in the second treatment surface 36 to be arched from its peripheral part, an edge portion 41 provided separated from the concave portion 38 on the second treatment surface 36, and a plain portion 42 provided separated from the concave portion 38 and opposite to the edge portion 41. The edge portion 41 (cavitation surface) linearly extends in a direction (width direction W) intersecting the longitudinal axis C of the probe 17 at the distal end of the treatment section 32. The edge portion 41 is provided adjacent to the concave portion 38, and has a shape that is elevated from the concave portion 38 toward the distal end side C1.

The first treatment surface 35 is curved along the curved surface of the concave portion 38. The outer peripheral portion 37 includes three side surfaces (end surfaces) provided between the first treatment surface 35 and the second treatment surface 36. In the present embodiment, the concave portion 38 is arched (a half cylinder extending in direction W intersecting the longitudinal axis C of the probe 17). However, the shape of the concave portion 38 is not limited to this, and may have a hemisphere shape, for example.

The coating portion 34 covers a part other than the edge portion 41 of the second treatment surface 36, the neck portion 33, and the probe main body 31. The coating portion 34 is made of a synthetic resin coating material, such as a polyether ether ketone (PEEK) coating material. The coating of the coating portion 34 is formed by liquid-painting or spray-coating a synthetic resin material on the part other than the edge portion 41 of the treatment section 32, the neck portion 33, and the probe main body 31. It is preferable to increase the surface roughness of the part on which the coating portion 34 is formed by performing surface treatment, such as sandblasting, in advance. This improves the adhesion strength between the probe 17 and the coating portion 34, and reduces the risk of the coating portion 34 detaching from the probe 17. In contrast, the edge portion 41 of the second treatment surface 36 is exposed to the outside, and can coagulate/incise body tissue by supplying a high-frequency current to the edge portion 41.

As shown in FIG. 1, the power source unit 13 includes an ultrasonic current supply section 26, a high-frequency current supply section 28 and an energy control section 43 that controls the ultrasonic current supply section 26 and the high-frequency current supply section 28. The energy control section 43 can control supply of an ultrasonic wave generation current from the ultrasonic current supply section 26 and supply of a high-frequency current from the high-frequency current supply section 28. The ultrasonic current supply section 26 and the high-frequency current supply section 28 are examples of the energy generation section. When a doctor operates an energy operation input button 21 (switch), an electrical signal is conveyed to the energy control section 43, and an input of an energy operation is detected. Accordingly, the energy control section 43 supplies an ultrasonic wave generation current from the ultrasonic current supply section 26 to the probe 17, and supplies a high-frequency current from the high-frequency current supply section 28 to the probe 17.

An operation of the treatment device 11 of the present embodiment will be described with reference to FIGS. 3 and 4. A doctor can operate the energy operation input button 21 with the second treatment surface 36 (edge portion 41) of the treatment section 32 brought into contact with body tissue. In this state, the edge portion 41 makes ultrasonic vibration, and applies a thermal energy of frictional motion to body tissue. Simultaneously, a high-frequency current flows from the edge portion 41 to body tissue, and an electrical energy can be thereby applied to the body tissue. Since two types of energies are applied from the treatment section 32 (edge portion 41), body tissue brought into contact with the edge portion 41 can be efficiently incised, and its peripheral tissue can be efficiently coagulated. The concave portion 38 and plain portion 42 around the edge portion 41 are covered by the coating portion 34. Therefore, even if those portions contact body tissue, a high-frequency current is prevented from flowing from those portions to body tissue.

A doctor can coagulate body tissue by operating the energy operation input button 21 with the first treatment surface 35 brought into contact with the body tissue. Accordingly, a treatment of stanching oozing blood can be performed on body tissue. In addition, the doctor can also incise/excise body tissue (in particular, membranous tissue, such as mesentery) by the outer peripheral portion 37 by operating the energy operation input button 21 with the outer peripheral portion 37 brought into contact with the body tissue.

According to the present embodiment, the treatment device 11 includes a probe 17 that conveys ultrasonic vibration and a high-frequency current; a treatment section 32 provided with a first treatment surface 35 provided at an distal end of the probe 17 for treating body tissue, a second treatment surface 36 opposed to the first treatment surface 35, and an outer peripheral portion 37 provided between the first treatment surface 35 and the second treatment surface 36 and configured to treat the body tissue with the ultrasonic vibration and the high-frequency current conveyed via the probe 17; and an electrically-insulating coating portion 34 that covers at least one of the first treatment surface 35 and the second treatment surface 36.

This configuration enables treatment of body tissue by the outer peripheral portion 37 and the part not covered by the coating portion 34 of the first treatment surface 35 and the second treatment surface 36.

The second treatment surface 36 includes a concave portion 38 and an edge portion 41 provided separated from the concave portion 38, and the coating portion 34 covers the second treatment surface 36 except for the edge portion 41. This configuration enables treatment of body tissue by the edge portion 41 because the edge portion 41 forms a part not covered by the coating portion 34. Since the second treatment surface 36 is covered with the coating portion 34 except for the edge portion 41, even if the part other than the edge portion 41 of the second treatment surface 36 comes into contact with body tissue, a high-frequency current can be prevented from flowing from the contact part to the body tissue. Accordingly, a minimally invasive treatment device 11 can be realized.

The treatment device 11 includes a neck portion 33 provided between the probe main body 31 and the treatment section 32 and having a dimension smaller than that of the treatment section 32 with respect to the width direction W intersecting the longitudinal axis C of the probe main body 31, and the coating portion 34 covers the neck portion 33 and the probe main body 31. This configuration realizes a minimally invasive treatment device 11 because provision of the neck portion 33 having a dimension smaller than that of the treatment section 32 makes the probe 17 difficult to contact body tissue at a part other than the treatment section 32. In addition, since the neck portion 33 and the probe main body 31 are covered with the coating portion 34, even if those portions are unintentionally brought into contact with body tissue, a high-frequency current does not flow from the portions to the body tissue, and a minimally invasive treatment device 11 can be realized.

Second Embodiment

A treatment device 11 of the second embodiment will be described with reference to FIGS. 5 and 6. The treatment device 11 of the second embodiment differs from that of the first embodiment in terms of the shape of the treatment section 32 and the part coated by the coating portion 34, but is identical thereto in the other respects. Therefore, mainly the parts different from those of the first embodiment will be described, and illustrations or descriptions of the parts identical to those of the first embodiment will be omitted.

The probe 17 includes a cylindrical (rod-shaped) probe main body 31, a treatment section 32 formed on the distal end side of the probe main body 31 integrally with the probe main body 31, and a coating portion 34 that covers at least a part of the treatment section 32. An O-ring 44 is interposed between the probe 17 and the sheath 18 to prevent liquid from entering the sheath 18.

As shown in FIG. 6, the treatment section 32 is a thin long plate having a distal end portion curved into an arc-like shape. The treatment section 32 includes a first treatment surface 35, a second treatment surface 36 opposed to the first treatment surface 35, and an outer peripheral portion 37 provided between the first treatment surface 35 and the second treatment surface 36 and adjacent to the first treatment surface 35 and the second treatment surface 36. The outer peripheral portion 37 literally surrounds the periphery of the treatment section 32, and is approximate inverted U-shaped.

The outer peripheral portion 37 includes an arc-like arched portion 45, and a pair of blade portions 46 linearly extending from the respective ends of the arched portion 45 to the proximal end side C2 of the longitudinal axis C of the probe main body 31. The arched portion 45 is curved to be concaved in a direction away from the probe main body (the proximal end side of the probe 17).

The coating portion 34 covers the first treatment surface 35, the second treatment surface 36, and the probe main body 31. The coating portion 34 is made of a synthetic resin coating material, such as a polyether ether ketone (PEEK) coating material. The coating of the coating portion 34 is formed by liquid-painting or spray-coating a synthetic resin material on the first treatment surface 35, the second treatment surface 36, and the probe main body 31. Surface treatment to increase surface roughness is performed on the part on which the coating portion 34 is formed. In contrast, the outer peripheral portion 37 is exposed to the outside, and can coagulate/incise body tissue.

An operation of the treatment device 11 of the present embodiment will be described with reference to FIGS. 5 and 6. A doctor can operate the energy operation input button 21 with a part of the outer peripheral portion 37 of the treatment section 32 brought into contact with body tissue. In this state, the outer peripheral portion 37 makes ultrasonic vibration, and applies a thermal energy of frictional motion to body tissue. Simultaneously, a high-frequency current flows from the outer peripheral portion 37 to body tissue, and an electrical energy can be thereby applied to the body tissue. Since two types of energies are applied from the treatment section 32 (outer peripheral portion 37), body tissue brought into contact with the outer peripheral portion 37 can be efficiently incised, and its peripheral tissue can be efficiently coagulated. The first treatment surface 35 and the second treatment surface 36 adjacent to the outer peripheral portion 37 are covered with the coating portion 34. Therefore, even if those portions contact body tissue, a high-frequency current is prevented from flowing from those portions to body tissue.

According to the present embodiment, in the treatment device 11, the treatment section 32 is shaped like a plate including a first treatment surface 35 and a second treatment surface 36 opposed to each other, and the outer peripheral portion 37 includes an arched portion 45 curved to be convex in a direction away from the probe main body 31, and a pair of blade portions 46 linearly extending from the respective ends of the arched portion 45 to the proximal end side of the longitudinal axis C of the probe main body 31. This configuration makes it possible to provide a convenient treatment device 11 capable of coagulating and incising body tissue at any part of the arched portion 45 and the pair of blade portions 46.

The coating portion 34 covers both the first treatment surface 35 and the second treatment surface 36. This configuration can prevent a high-frequency current from flowing from the first treatment surface 35 and the second treatment surface 36 to body tissue, and can realize a minimally invasive treatment device 11.

Third Embodiment

A treatment device 11 of the third embodiment will be described with reference to FIGS. 7 to 9. The treatment device 11 of the third embodiment differs from that of the second embodiment in that the coating section 34 does not cover the first treatment surface 35, but is identical thereto in the other respects. Therefore, mainly the parts different from those of the second embodiment will be described, and illustrations or descriptions of the parts identical to those of the second embodiment will be omitted.

Figure 9:
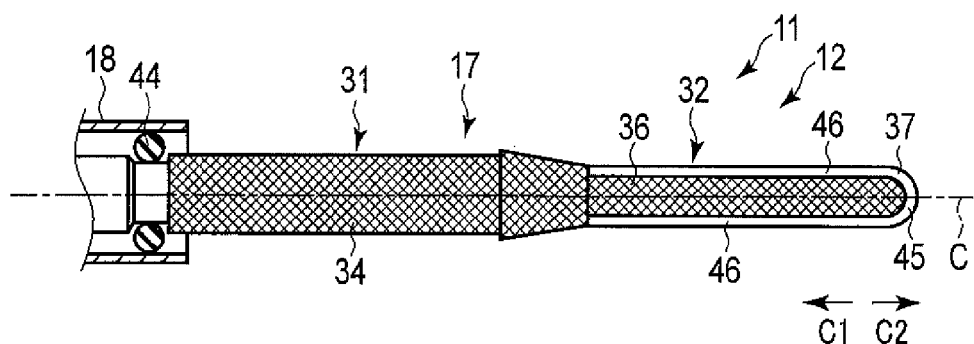
FIG. 9 is a right-side view showing the probe of the treatment device shown in FIG. 8.

In the present embodiment, the coating portion 34 covers the second treatment surface 36 and the probe main body 31, as shown in FIG. 9. The coating portion 34 is made of a synthetic resin coating material, such as a polyether ether ketone (PEEK) coating material. The coating of the coating portion 34 is formed by liquid-painting or spray-coating a synthetic resin material on the second treatment surface 36 and the probe main body 31.

Figure 8:
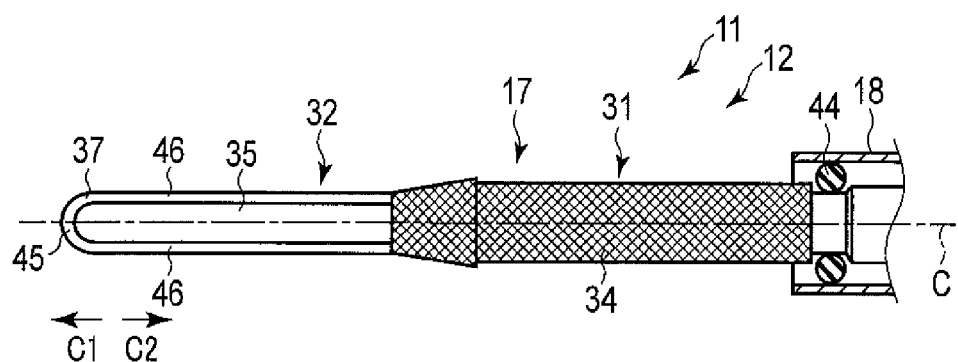
FIG. 8 is a left-side view showing the probe of the treatment device shown in FIG. 7.

As shown in FIG. 8, the first treatment surface 35 and the outer peripheral portion 37 are exposed to the outside, and can coagulate and incise body tissue.

An operation of the treatment device 11 of the present embodiment will be described with reference to FIGS. 7 to 9. A doctor can operate the energy operation input button 21 with a part of the outer peripheral portion 37 of the treatment section 32 brought into contact with body tissue. In this state, the outer peripheral portion 37 makes ultrasonic vibration, and applies a thermal energy of frictional motion to body tissue. Simultaneously, a high-frequency current flows from the outer peripheral portion 37 to body tissue, and an electric energy can be thereby applied to the body tissue. Since two types of energies are applied from the treatment section 32 (outer peripheral portion 37), body tissue brought into contact with the outer peripheral portion 37 can be efficiently incised, and its peripheral tissue can be efficiently coagulated.

A doctor can coagulate body tissue by operating the energy operation input button 21 with the first treatment surface 35 brought into contact with the body tissue. Accordingly, a treatment of stanching oozing blood can be performed on body tissue.

According to the third embodiment, since the insulating coating portion 34 covers the second treatment surface 36, even if the second treatment surface 36 is unintentionally brought into contact with body tissue during treatment, a high-frequency current does not flow from that part, and a minimally invasive treatment device 11 can be realized.

Next, a modification (first modification and second modification) of the treatment device 11 of each of the second embodiment and the third embodiment will be described with reference to FIG. 10. In the first modification, a part of the outer peripheral portion 37 of the treatment device 11 of the second embodiment is covered with the coating portion 34 (see FIG. 10). Specifically, one of the pair of blade portions 46 in the outer peripheral portion 37 is covered with the coating portion 34. The other parts of the configuration are the same as those of the treatment device 11 of the second embodiment.

Figure 10:
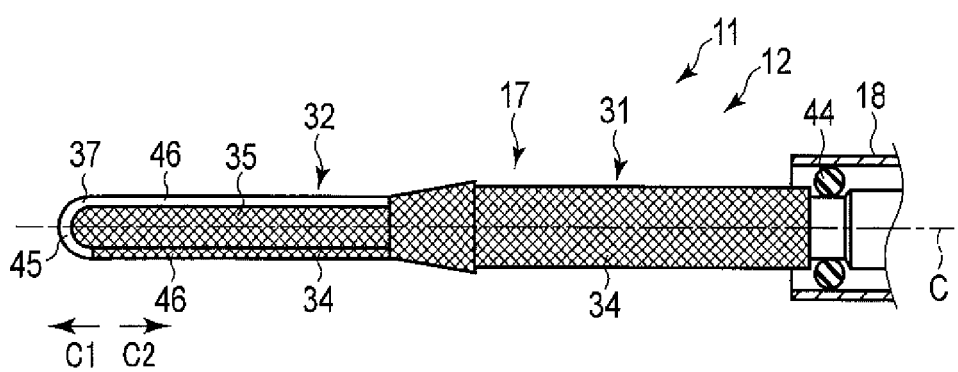
FIG. 10 is a side view showing a modification of the treatment device of the second embodiment and a modification of the treatment device of the third embodiment.

In the second modification, a part of the outer peripheral portion 37 of the treatment device 11 of the third embodiment is covered with the coating portion 34 as in the first modification shown in FIG. 10. Specifically, one of the pair of blade portions 46 in the outer peripheral portion 37 is covered with the coating portion 34. The other parts of the configuration are the same as those of the treatment device 11 of the third embodiment.

The first modification and the second modification can prevent a high-frequency current from flowing to body tissue not to be treated when a blade portion 46 on the opposite side to the treatment side comes into contact with body tissue, for example, in treatment in a narrow hole. Thereby a minimally invasive treatment device 11 can be realized.

The present invention is not limited to the above-described embodiments, and can be appropriately modified in practice, without departing from the gist of the invention. In addition, one treatment device may be configured by a combination of the treatment devices of the above-described embodiments, as a matter of course.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device for use with body tissue, the treatment device comprising:
    an ultrasonic transducer configured to generate ultrasonic vibration;
    a probe configured to transmit the ultrasonic vibration and a high-frequency current;
    a treatment section at a distal end of the probe, the treatment section having a first treatment surface and a second treatment surface, and the treatment section being configured to treat the body tissue with the ultrasonic vibration and the high-frequency current that is transmitted to the first treatment surface and the second treatment surface via the probe,
    the second treatment surface including:
        a plain portion opposed to the first treatment surface,
        a concave portion adjacent to the plain portion in a distal end direction, the concave portion being concave towards the first treatment surface and forming a profile of cylinder extending in a direction intersecting a longitudinal direction of the probe, and
        an edge portion adjacent to the concave portion in the distal end direction and being exposed to allow the high-frequency current to electrically flow;
    an electrically-insulating coating portion covering the plain portion and the concave portion of the second treatment surface; and
    an outer peripheral portion corresponding to a side surface of the treatment section positioned between the first treatment surface and the second treatment surface, is exposed to allow the high-frequency current to electrically flow to the body tissue such that the body tissue is treated with the high-frequency current, wherein
    the concave portion has a half-cylinder shape extending in a direction intersecting a longitudinal axis of a probe main body of the probe.

2. The treatment device of claim 1, further comprising:
    a neck portion provided between a probe main body and the treatment section and having a dimension smaller than that of the treatment section with respect to a width direction intersecting a longitudinal axis of the probe main body, wherein
    the electrically-insulating coating portion covers the neck portion and the probe main body.

3. The treatment device of claim 1, wherein the electrically-insulating coating portion covers at least a part of the outer peripheral portion.

4. The treatment device of claim 1, wherein the electrically-insulating coating portion covers the first treatment surface.

5. The treatment device of claim 1, wherein the treatment section is shaped like a spoon or spatula.

6. The treatment device of claim 1, wherein the edge portion is elevated from the concave portion of the second treatment surface in a direction away from the first treatment surface.

7. A treatment device comprising:
- an ultrasonic transducer configured to generate ultrasonic vibration;
- a probe configured to transmit ultrasonic vibration and a high-frequency current;
- a treatment section having: (A) a first treatment surface provided at a distal end of the probe, and (B) a second treatment surface, the treatment section being configured to treat the body tissue with the ultrasonic vibration and the high-frequency current that is transmitted to the first treatment surface and the second treatment surface via the probe,
  the first treatment surface and the second treatment surface being plates opposed to each other,
  the second treatment surface including:
    - a plain portion opposed to the first treatment surface,
    - a concave portion adjacent to the plain portion in a distal end direction, the concave portion being concave towards the first treatment surface and forming a profile of cylinder extending in a direction intersecting a longitudinal direction of the probe, and
    - an edge portion adjacent to the concave portion in the distal end direction and being exposed to allow the high-frequency current to electrically flow;
- a neck portion provided between a probe main body of the probe and the treatment section and having a dimension smaller than that of the treatment section with respect to a width direction intersecting a longitudinal axis of the probe main body;
- an electrically-insulating coating portion covering the first treatment surface and the plain portion and the concave portion of the second treatment surface as well as the neck portion and the probe main body; and
- an outer peripheral portion forming a side surface of the treatment section between the first treatment surface and the second treatment surface, the outer peripheral portion being exposed to allow high-frequency current to electrically flow to the body tissue such that the body tissue is treated with the high-frequency current, wherein
- the concave portion has a half-cylinder shape extending in a direction intersecting a longitudinal axis of a probe main body of the probe.

8. The treatment device of claim 7, wherein the edge portion is elevated from the concave portion of the second treatment surface in a direction away from the first treatment surface.

* * * * *